United States Patent [19]

Maitland

[11] Patent Number: 4,696,646
[45] Date of Patent: Sep. 29, 1987

[54] DENTAL WEDGE AND METHOD OF USING SAME

[76] Inventor: Ronald I. Maitland, 155 East Fifty-fifth St., New York, N.Y. 10022

[21] Appl. No.: 812,350

[22] Filed: Dec. 23, 1985

[51] Int. Cl.[4] ............................................. A61C 7/00
[52] U.S. Cl. .................................... 433/149; 433/229
[58] Field of Search .................. 433/149, 229, 141, 29

[56] References Cited

U.S. PATENT DOCUMENTS

| | | | |
|---|---|---|---|
| 3,193,094 | 7/1965 | Schulstad | 433/149 |
| 3,473,226 | 10/1969 | Arlers et al. | 433/149 |
| 4,608,021 | 8/1986 | Barrett | 433/229 |
| 4,631,030 | 12/1986 | von Weissenflut | 433/229 |

Primary Examiner—John J. Wilson
Attorney, Agent, or Firm—Cooper, Dunham, Griffin & Moran

[57] ABSTRACT

The subject invention is a device for use in composite resin dental restoration and a method for overcoming the difficulty of establishing sufficient separation to provide firm and properly located interproximal contact. This invention creates an easy, predictable method for establishing proper interproximal contact pressure and anatomical form. The wedge is used in a method which establishes predicatable interproximal static contour relationships with matrix systems, providing the necessary additional interproximal separation and reducing the thickness of the composite resin to be cured by light catalysis to insure more complete curing in the deeper recesses in the cavity preparation.

24 Claims, 11 Drawing Figures

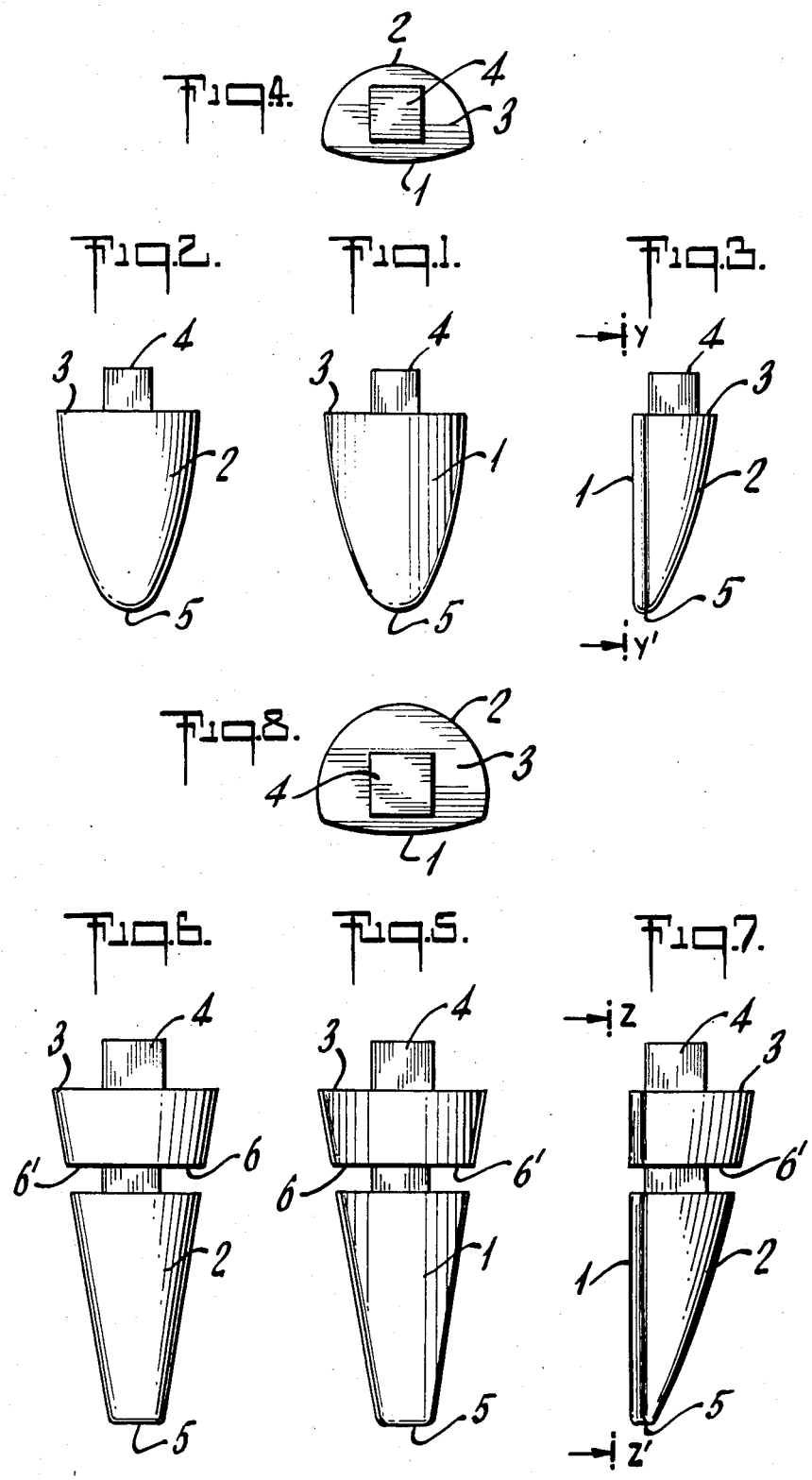

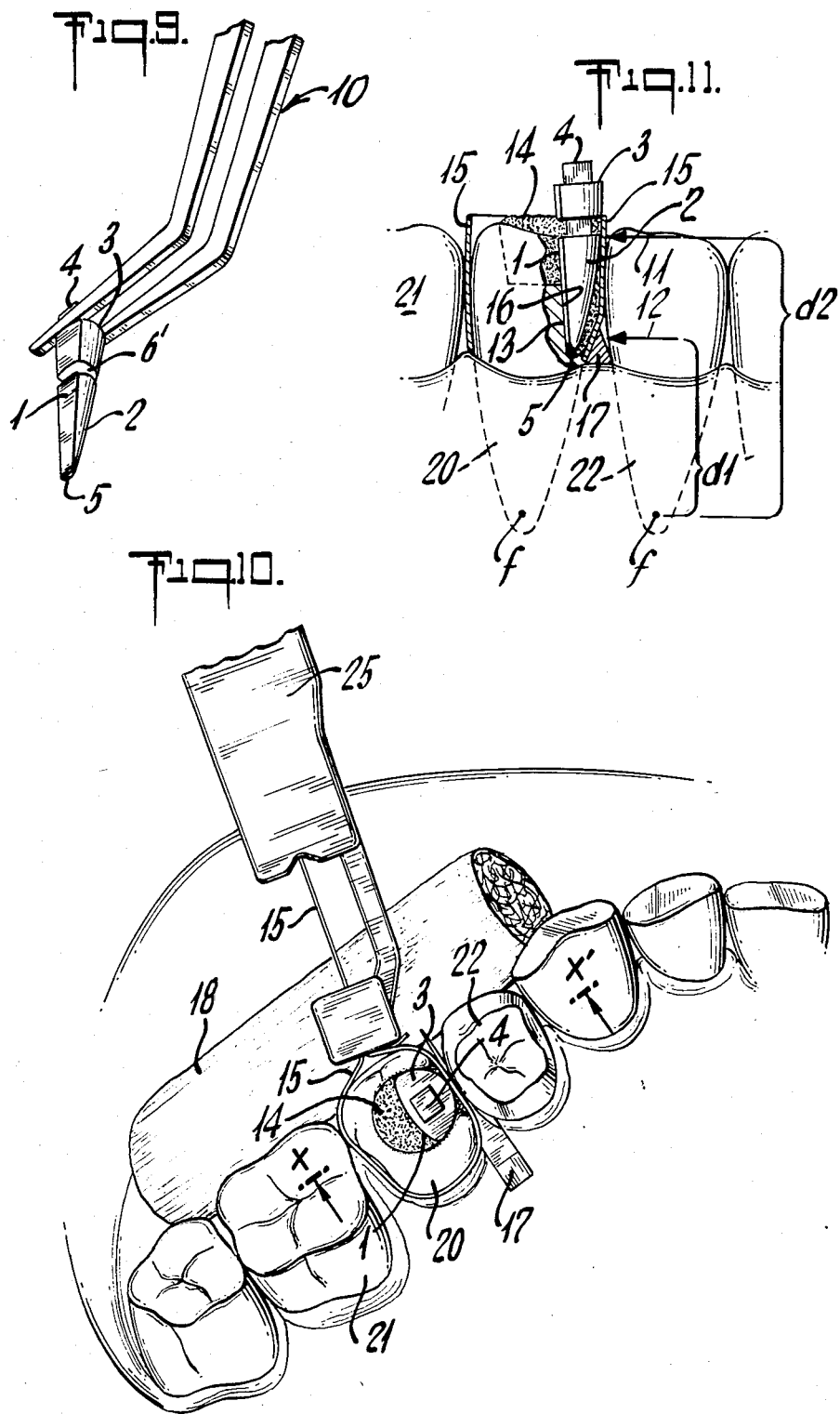

DENTAL WEDGE AND METHOD OF USING SAME

FIELD OF THE INVENTION

This invention pertains to a device for assisting in dental restoration and to a method of using the device in composite resin dental restoration to establish a firm and properly located interproximal contact relationship.

BACKGROUND OF THE INVENTION

The recent technological revolution in cosmetic bonding for dental restorations has provided a myriad of ceramic-resin systems. Materials have become more sophisticated, exhibiting better resistance to wear, better crushing strength, and better ability to seal or bond to both enamel and dentin tooth structure.

The restorative composite resin materials that are used for posterior dental restoration include a Bis GMA resin or urethane dimethacrylate resin with various sized and shaped hard filler particles of ceramic, quartz or glass material. The hard filler particles presently being used include: quartz, barium glass, silica glass, agglomerated silica complexes, silica pellets, zeolite, strontium glass, RCMS (resin capped micro silica), barium aluminum silicate glass, lithium aluminum silicate glass and zinc glass. The percent load of hard filler material varies according to particle size, shape and manufacturers' specifications.

Many problems in the use of these materials in the posterior regions of the mouth have been overcome. Prior to this invention a perplexing problem has continued to exist in establishing firm and properly located interproximal contact when using the new composite ceramic-resin technology, in spite of the various innovative matrix systems which recently have been developed.

During fabrication and insertion of a dental restoration with composite ceramic-resin materials, a matrix band is used to hold the restorative material within a cavity prepared in the tooth being restored. A gingival wedge commonly is used with the matrix band to force the adjacent teeth apart and to hold the matrix band tightly against the tooth being restored, at the gum line. The restorative material is then inserted and hardened, and afterwards the matrix band is removed. However, when the matrix band and gingival wedge are removed and the separation pressure is relieved, a space may remain between the restoration and the adjacent tooth. Food particles become lodged in that space and eventually cause tooth decay and/or gum disease.

Conventional matrix and wedging techniques call for very thin matrix bands and various forms of extra coronal gingival wedges. The separation afforded by gingival wedge pressure has been thought to overcome the interproximal gap created by the matrix band after restoration is complete. In spite of ever thinner matrices (0.0015 or 0.0010 inches), subsequent to composite restoration, weak or open contact has been common.

Food particles can collect in these spaces. Additionally, the plasticity of the composite materials before curing makes it difficult to obtain the desired contour of the restored tooth. The composite materials may be self-curing or light-cured. However, with the preferred light-cured composites, it is sometimes difficult to cure the composite material in the deeper recesses of the cavity.

Further, studies of wedge efficiency and separation show that the most common brands of wooden wedges experience wedge fatigue, with corresponding loss of original apparent separation, after only about four minutes of use. Unyielding plastic or other wedges made from hard non-compressible materials are more efficient separators and do not fatigue, but often do not "grip" well and slide or loosen during tooth and restorative manipulation. Hard, non-yielding and non-fatiguing wedges also do not properly hold the matrix well against the irregular cervical root anatomy. As a result, use of these hard wedges allows overhangs and poor gingival margin adaptation in the cured restoration.

In contrast to composite resin restoration, traditional silver amalgam restoration, when inserted after proper gingival wedging, provides auxiliary wedging and separation. The auxiliary wedging and separation of the amalgam restoration is due to the compactibility of the amalgam and its ability to stay where it is placed and to be condensed with significant pressure causing a lateral force vector against the adjacent tooth. This additional separation is crucial to establishing a successful contact, which is routinely obtained in amalgam restorative systems. The currently available composite resin techniques heretofore do not allow such routine success. Table 1 shows a typical test result using a wooden gingival wedge and silver amalgam. Prior to this invention, auxiliary wedging was not possible through condensation of composite resin materials, no matter how highly filled or stiff these materials have been.

Accordingly, it is an object of this invention to provide a device which will establish firm and properly located interproximal contact relationships with composite resin restorative materials.

A further object of this invention is to provide an easy, predictable method for establishing proper interproximal contact pressure and anatomic form with a composite resin restoration.

Another object of this invention is to provide a device for establishing static contour relationships with matrix systems to provide the necessary interproximal separation when using composite resin restorative material.

An additional object of this invention is to provide a device which reduces the thickness of the composite resin material to be cured by light catalysis in order to insure more complete curing of the deeper recesses of the cavity preparation.

Additionally, a further object of this invention is to decrease the bulk of restorative resin to be cured to eliminate the disadvantages inherent in linear and volumetric shrinkage of the material during setting.

TABLE 1

| Test Results Using Wooden Gingival Wedge and Silver Amalgam (See FIG. 9) | | |
|---|---|---|
| STEP | INTER-PROXIMAL SEPARATION (INCHES) | COMMENTS |
| Separation at initial reference point (11) | 0.0000 | |
| Separation after wooden wedge inserted | +0.0010 | |
| After 4 minutes with wooden wedge | +0.0006 | Teeth moved closer |
| After teeth are rewedged forcefully | +0.0013 | More separation |

TABLE 1-continued

Test Results Using Wooden Gingival Wedge and Silver Amalgam (See FIG. 9)

| STEP | INTER-PROXIMAL SEPARATION (INCHES) | COMMENTS |
|---|---|---|
| After amalgam has been inserted and condensed/packed into the cavity of packing | +0.0019 | Lateral component of forces transferred from packing instrument to the amalgam pushes on side of adjacent tooth causing more separation, restored tooth moves away from adjacent tooth |
| After wedge removed | +0.0003 | Close to optimum separation slight over contact pressure allows strip finishing |

SUMMARY OF THE INVENTION

The subject invention relates to a device for use with composite resin dental restorations and to a method for overcoming the difficulty of establishing firm contact and properly located interproximal contour. This invention creates an easy, predictable technique for establishing proper interproximal contact pressure and anatomic form. The device is used in a method which establishes predictable interproximal static contour relationships with matrix systems. The device and method provide the necessary additional interproximal separation and also reduces the thickness of the composite resin material to be cured by light catalysis to insure more complete curing of the deeper recesses of the cavity preparation. As it is fabricated from the same type of composite resin material as the restoration itself, the device becomes incorporated into the final restoration and in fact is the central core of the proximal segment of the restoration. Occlusal excess is easily carved away with burs and diamond stones after the restoration has been cured.

The introduction of a wedge of hard, already cured composite resin into a sea of uncured restorative material in the proximal area acts as a plunger to insure tight and complete adaptation of the restorative material to the etched and bonded receptor surfaces of the cavity. This enhanced adaptation aids in increasing the surface bonding of the restorative material to the tooth structure. Furthermore, use of the device reduces curing shrinkage and saves on the cost of restorative material, since less restorative material is used. The reduction of the dimensional shrinkage during curing allows for a better seal of the restorative material to the tooth and eliminates the strains on the natural tooth which would be caused by a volumetric change. The device is easily custom fitted and inserted to fit most restorative situations. A denser, better retained and better fitting restoration results. Accordingly, use of the device in the method of this invention results in a similar interproximal separation with composite materials as previously obtained with silver amalgam restoration (see Table 1. Final finishing can be accomplished for a properly-contoured and smooth result with no compromise on contact firmness.

By using this device, the dentist can now end up with contact pressure sufficiently firm to allow for some removal at the contact point for fine finishing and smoothness of interproximal contour. Prior to the invention of this device, all contact that was able to be obtained was crucial and further finishing made wider gaps between the teeth. The older technique encouraged poorly finished, rough interproximal areas which enhanced the detrimental plaque and food accumulation.

These and other advantages of this invention will become apparent from the following description when read with reference to the accompanying drawings.

BRIEF DESCRIPTION OF THE DRAWINGS

FIG. 1 is a side elevation view of a first embodiment of the device facing the substantially planar side (1).

FIG. 2 is a side elevational view of a first embodiment of the device facing the substantially rounded side (2).

FIG. 3 is a front elevational view of a first embodiment of the device taken facing towards the line Y—Y' of FIG. 1.

FIG. 4 is a top plan view of a first embodiment of the device facing the broad top portion (3) and the small protrusion (4).

FIG. 5 is a side elevation view of a second embodiment of the device facing the substantially planar side (1).

FIG. 6 is a side elevational view of a second embodiment of the device facing the substantially rounded side (2).

FIG. 7 is a front elevational view of a second embodiment of the device taken facing towards the line Z—Z' of FIG. 5.

FIG. 8 is a top plan view of a second embodiment of the device facing the broad top portion (3) and the small protrusion (4).

FIG. 9 is a perspective view of a second embodiment of the device being grasped at protrusion (4) by an implement.

FIG. 10 is a bottom plan view of the upper jaw showing a tooth being restored using the device.

FIG. 11 is a partial cutaway, inverted elevational view of the upper jaw taken along the line X—X' of FIG. 10, showing a tooth being partially cut away along the line.

DETAILED DESCRIPTION OF THE INVENTION

This invention relates to a device for dental restoration as shown in FIGS. 1-11, which assures sufficient separation to provide firm and properly located interproximal contact. The device comprises a wedge of cured restorative composite resin, such as, a Bis GMA resin filled with hard filler material, or a urethane dimethacrylate resin filled with the same hard filler material. The hard filler material includes ceramic, quartz or glass particles. The hard filler particles presently being used include: quartz, barium glass, silica glass, agglomerated silica complexes, silica pellets, zeolite, strontium glass, RCMS (resin capped micro silica), barium aluminum silicate glass, lithium aluminum silicate glass and zinc glass. The percent load of hard filler material varies according to particle size, shape and manufacturers' specifications.

The wedge is adapted for insertion into a prepared cavity (13) within a tooth (20). The wedge is shaped to frictionally engage the axial interproximal wall (16) of the cavity (13) and the proximal surface of the adjacent tooth (22). Uncured restorative composite resin (14) surrounds the wedge and is cured after the wedge is inserted into the cavity containing the uncured soft resin. The final cured restoration incorporating the composite resin and wedge then can be finished to an appropriate anatomical shape.

The wedge is generally cone-shaped (see FIGS. 3 and 7) to frictionally engage the wall of a standard interproximal box shaped cavity (13). Preferably, the wedge has two elongated sides (1 and 2), one elongated side being substantially planar (1) and the other elongated side being substantially rounded (2). Desirably, the substantially planar side (1) is slightly convex. The wedge has a broad top portion (3) and a narrow bottom portion (5). The bottom portion (5) is adapted to be inserted into the cavity (13) and the top portion (3) includes a small protrusion (4) which is adapted to be grasped by an implement (10).

When inserted into the cavity (13), the substantially rounded side (2) is adapted to frictionally engage a matrix band (15) wrapped around the tooth (20), forcing the matrix band against the adjacent tooth (22), and the substantially planar side (1) is adapted to frictionally engage the axial wall (16) within the cavity (13). The wedge can be made in different sizes and shapes for different sized teeth and to fit the shape of different cavities. In a one embodiment (FIGS. 5–8 and FIG. 11) the top portion has at least one score line (6–6' at which a part of the broad top portion (3) can broken off after the uncured restorative composite resin (14) is cured.

Optimum benefit of this invention is obtained by inserting the fully cured hard wedge between the axial cavity wall and the matrix band resting against an adjacent tooth (22). The technique dictates that the filler particles used in the wedge resin be either unpigmented (clear) or having a very light pigmentation. In this way light catalysis is enhanced by transmitting light along the wedge into the deepest recesses of the prepared cavity (13) and aiding in the curing process of the uncured restorative resin previously inserted into the prepared cavity (13).

This invention also relates to a method for dental restoration using a restorative composite resin, which assures sufficient separation to provide firm and properly located interproximal contact. The method comprises the following steps:

(a) Cleaning the tooth to be restored.

(b) Selecting an appropriate shade of restorative composite resin matching the color of the tooth.

(c) Isolating the tooth from the gums, tongue and other sources of moisture by use of an appropriate barrier or dam (18).

(d) Separating the tooth from adjacent teeth by inserting, from the inside of the mouth (lingual side), at least one gingival wedge (17), preferably made from wood, between the tooth to be restored (20) and the adjacent teeth (21, 22) to provide sufficient space for insertion of a matrix band (15).

(e) Isolating the tooth (20) with a matrix band (15) which may held by a suitable implement (25), and securing the band with a gingival wedge (17), preferably made from wood.

(f) Preparing a cavity (13) in the tooth (20).

(g) Protecting exposed dentin by covering with a layer of acid resistant material, such as calcium hydroxide.

(h) Placing a suitable cement base, such as a glass ionomer cement, to build the inside of the prepared cavity to an ideal anatomical structure.

(i) Etching the enamel portion of the prepared cavity and the cement base surface for a sufficient time with an etchant.

(j) Removin9 the etchant, acid resistant material and other debris, and drying the etched tooth.

(k) Coating the etched cavity with a layer of bonding agent.

(l) Inserting a shaped wedge of cured restorative composite resin, such as the wedge of the present invention, into the cavity (13). The wedge is inserted to engage within the cavity so that the substantially rounded side (2) frictionally engages the matrix band (15), forcing the matrix band against the adjacent tooth (22), and the substantially planar side (1) frictionally engages an axial interproximal wall (16) of the cavity (13). This arrangement is to provide auxiliary wedging and to assure sufficient separation to provide firm and properly located interproximal contact in the finished restoration, which is located between teeth (20) and (22) at a point (11) (see FIGS. 10 and 11).

(m) Removing the wedge material after verifying a tight frictional fit.

(n) Filling the cavity (13) with an uncured restorative composite resin (14).

(o) Reinserting the wedge to the previous proper position and trimming the excess of uncured restorative composite resin.

(p) Curing the uncured restorative composite resin around the wedge.

(q) Removing the matrix band (15) and gingival wedge (17).

(r) Removing excess cured restorative composite resin, carving and polishing the restoration to ideal anatomy and smoothness to finish the restoration.

By following this method, the tooth (20) is restored to its original shape and proper interproximal contact is maintained. As is known to those skilled in dental restoration, one or more of the foregoing steps may not be necessary in all cases.

More specifically, this invention is an improved method for dental restoration using a restorative composite resin which assures sufficient separation to provide firm and properly located interproximal contact. The improvement comprises the following preferred steps:

(a) Inserting a shaped wedge of cured restorative composite resin into a prepared cavity. The wedge is shaped to frictionally engage the axial wall (16) of an interproximal box shaped cavity (13). The wedge has two elongated sides (1 and 2). The cavity (13) is prepared to be filled with an uncured restorative composite resin (14) in a tooth (20) isolated with a matrix band (15). Desirably, the substantially rounded side (2) of the wedge frictionally engages the matrix band (15), forcing the matrix band (15) against an adjacent tooth (22), while the substantially planar side (1) of the wedge frictionally engages an axial wall (16) within the interproximal box of the prepared cavity (13), providing auxiliary wedging and assuring sufficient separation to provide firm and properly located interproximal contact in the finished restoration.

(b) Removing the wedge after verifying that a tight frictional fit has been obtained.

(c) Filling the prepared cavity (13) with the uncured restorative composite resin (14).

(d) Reinserting the wedge to the previous proper position and trimming the excess uncured restorative composite resin.

(e) Curing the restorative composite resin.

(f) Removing the excess cured restorative composite resin, carving and polishing the restoration to an ideal anatomy and smoothness to finish the restoration. In a one embodiment of the wedge, a part of the top portion (3) of the wedge is broken off at a score line (6-6') after the uncured resin is cured. The amount of force (F2) needed for a wedge to separate the proximal teeth (20 and 22 as shown in FIG. 11) may be calculated for the needed interproximal separation by dividing the desired separation distance (at 11) by the distance (d2), from that point to the fulcrum (f). The force (F2) is smaller than the amount of force (F1) needed to separate the proximal teeth (20 and 22) at the gum line by using a gingival wedge. The force (F1) may be calculated by dividing the amount of gingival separation (at 12) by the distance (d1) from the point (12) to the fulcrum (f). It is readily calculable that the force (F2) at (11) is less than the force (F1) at (12). Accordingly, less force is needed to separate proximal teeth (20 and 22) at (11) by the wedge of the invention than is required to separate the teeth by using the gingival wedge at (12). Use of a wedge at (11) together with a gingival wedge at (12) alleviates the pressure that causes gingival wedge fatigue and loss of original apparent separation experienced in prior composite resin dental restoration techniques.

Although the above description is of the preferred embodiments of the invention, many modifications which are within the spirit and scope of the invention will be apparent to those skilled in the art.

I claim:

1. A device for dental restoration which assures sufficient separation to provide firm and properly located interproximal contact, comprising a wedge of highly crush resistant and wear resistant dental cured restorative composite resin for insertion into a prepared cavity within a tooth adapted to be filled with uncured restorative composite resin, the wedge being shaped to frictionally engage at least one wall of the cavity so that the wedge can be inserted into the uncured resin where said wedge remains, the uncured resin containing the wedge can be cured, and the cured resin can be finished to an appropriate anatomical shape.

2. The device of claim 1, wherein the wedge is shaped to frictionally engage an axial wall of the cavity which is prepared in the shape of an interproximal box.

3. The device of claim 1, wherein the wedge has two elongated sides, one elongated side being substantially planar and the other elongated side being substantially rounded.

4. The device of claim 3, wherein the substantially planar side is slightly convex.

5. The device of claim 3, in which the substantially rounded side is adapted to frictionally engage a matrix band wrapped around the tooth, forcing the matrix band against the adjacent tooth, and the substantially planar side is adapted to frictionally engaged the axial wall within the cavity.

6. The device of claim 1, further comprising a broad top portion and a narrow bottom portion wherein the bottom portion is adapted to be inserted into the cavity and the top portion is adapted to be grasped.

7. The device of claim 6, wherein the top portion includes a small protrusion.

8. The device of claim 6, wherein the top portion has at least one score line at which a part of the broad top portion can be broken off after the uncured restorative composite resin is cured.

9. The device of claim 1, wherein the restorative composite is a Bis GMA resin filed with hard filler particles.

10. The device of claim 9, wherein the hard filler particles are selected from a group which includes: quartz, barium glass, silica glass, agglomerated silica complexes, silica pellets, zeolite, strontium glass, RCMS (resin capped micro silica), barium aluminum silicate glass, lithium aluminum silicate glass and zinc glass.

11. The device of claim 9, wherein the hard filler particles are positioned at a higher concentration toward the center of the wedge, and are selected so as to form a solid wedge component which acts to allow direction and transmission of light along the wedge into the cavity to enhance the curing of the uncured restorative composite resin by light catalysis.

12. The device of claim 1, wherein the restorative composite resin is a urethan dimethacrylate resin filled with hard filler particles.

13. The device of claim 12, wherein the hard filler particles are selected from a group which includes: quartz, barium glass, silica glass, agglomerated silica complexes, silica pellets, zeolite, strontium glass, RCMS (resin capped micro silica), barium aluminum silicate glass, lithium aluminum silicate glass and zinc glass.

14. The device of claim 12, wherein the hard filler particles are selected so as to allow transmission of light along the wedge into the cavity to enhance the curing of the uncured restorative composite resin by light catalysis.

15. The device of claim 1, wherein said wedge of cured restorative composite resin comprises a metal silicate glass.

16. An improved method for dental restoration using a restorative composite resin which assures sufficient separation to provide firm and properly located interproximal contact, in which the improvement comprises:

(a) inerting a shaped wedge of cured restorative composite resin into a prepared cavity adapted to be filled with an uncured restoration composite resin in a tooth, such that the shaped wedge is frictionally engaged within the cavity and against an adjacent tooth;

(b) removing the wedge vertifying tight frictional fit;

(c) filling the prepared cavity with the uncured restorative composite resin;

(d) reinserting the wedge into its previous proper position, where it remains and becomes part of the restored tooth, and trimming the excess uncured restorative composite resin;

(e) curing the uncured restorative composite resin containing the wedge; and (f) removing excess cured restorative composite resin, carving and polishing the restoration to ideal anatomy and smoothness to finish the restoration so that the tooth is restored to its original shape and proper interproximal contact is maintained.

17. The method of claim 16, further comprising frictionally engaging the wedge with an axial wall of an interproximal box shaped cavity.

18. The method of claim 16, in which the wedge has two elongated sides, one side being substantially planar and the other side being substantially rounded.

19. The method of claim 18, further comprising frictionally engaging a matrix band which isolates the tooth, with the substantially rounded side of the wedge, forcing the matrix band against the adjacent tooth, and frictionally engaging an axial interproximal wall within the cavity with the substantially planar side of the wedge to provide auxiliary wedging and assure sufficient separation to provide firm and properly located interproximal contact in the finished restoration.

20. The method of claim 16, wherein said shaped wedge of curd restorative composite resin comprises a metal silicate glass.

21. An improved method for dental restoration using a restorative composite resin which assures sufficient separation to provide firm and properly located interproximal contact, in which the imrpovement comprises:
   (a) inserting a shaped wedge of cured restorative composite resin into a prepared cavity adapted to be filled with an uncured restorative composite resin in a tooth, such that the shaped wedge is frictionally engaged within the cavity and against an adjacent tooth:
   (b) removing the wedge verifying tight frictional fit;
   (c) filling the prepared cavity with the uncured restorative composite resin;
   (d) reinserting the wedge into its previous proper position, where it remains and becomes part of the restored tooth, and trimming the excess uncured restorative composite resin;
   (e) curing the uncured restorative composite resin containing the wege;
   (f) removing excess cured restorative composite resin, carving and polishing the restoration to ideal anatomy and smoothness to finish the restoration so that the tooth is restored to its original shape and proper interproximal contact is maintained; and
   (g) breaking off a part of the top portion of the shaped wedge after the uncured restorative composite resin is cured.

22. A method for dental restoration using a restorative composite resin which assures sufficient separation to provide firm and properly located interproximal contact, comprising the folliwng steps:
   (a) cleaning the tooth to be restored;
   (b) selecting an approxiate shade of restorative composite resin matching the color of the tooth;
   (c) isolating the tooth from the gums, tongue and other sources of moisture;
   (d) separating the tooth from adjacent teeth by inserting a gingival wedge between the tooth to be restored and the adjacent teeth to provide sufficient space for insertion of a matrix band;
   (e) isolating the tooth with a matrix band and securing the band with a gingival wedge;
   (f) preparing a cavity in the tooth;
   (g) protecting exposed dentin by covering with a layer of acid resistant material;
   (h) placing a cement base in the cavity to build the inside of the prepared cavity to an ideal anatomical structure;
   (i) etching the enamel portion of the prepared cavity and the cement base for a sufficient time with an etchant;
   (j) removing the etchant, acid resistant mateerial and other debris, and drying the etched tooth;
   (k) coating the etched cavity with a layer of bonding agent;
   (1) filling the cavity with an uncured restorative composite resin;
   (m) inserting a shaped wedge of cured restorative composite resin into the cavity, frictionally engaging the wedge within the cavity so that the wedge engages the matrix band, forcing the matrix band against the adjacent tooth, so that the wedge also engages an axial interproximal wall within the cavity to provide auxiliary wedging and assure sufficient separation to provide firm and properly located interproximal contact in the finished restoration and leaving the wedge so engaged within the cavity;
   (n) trimming the excess uncured restorative composite resin;
   (o) curing the uncured restorative composite resin together with the shaped wedge;
   (p) removing the matrix band and gingival wedge; and
   (q) removing excess cured restorative composite resin, carving and polishing the restoration to an ideal anatomy and smoothness to finish the restoration, so that the tooth is restored to its original shape and proper interproximal contact is maintained.

23. The method of claim 22, wherein said shaped wedge of cured restorative composite resin comprises a metal siliate glass.

24. A device for dental restoration which assures sufficient separation to provide firm and properly located interproximal contact, comprising a wedge comprising highly crush resistant and wear resistant dental metal silicate glass forinsertion into a prepared cavity within a tooth adapted to be filled with uncured restorative composite resin, the wedge being shaped to frictionally engage at least one wall ofthe cavity so that the wedge can be inserted into the uncured resin and cured, and the cured resin and wedge can be finished to an approxiate anatomical shape.

* * * * *